United States Patent [19]
Moore et al.

[11] Patent Number: 5,424,840
[45] Date of Patent: Jun. 13, 1995

[54] IN SITU CHLOROPHYL ABSORPTION METER

[75] Inventors: Casey Moore, Philomath; J. Ronald V. Zaneveld, Corvallis, both of Oreg.

[73] Assignee: The State of Oregon Acting by and through the State Board of Higher Education on Behalf of Oregon State University, Corvallis, Oreg.

[21] Appl. No.: 285,486

[22] Filed: Aug. 3, 1994

Related U.S. Application Data

[63] Continuation of Ser. No. 918,529, Jul. 21, 1992, abandoned.

[51] Int. Cl.⁶ .................. G01N 21/85; G01N 15/06; G01N 1/00
[52] U.S. Cl. .................. 356/410; 356/419; 356/440; 250/573; 250/576; 73/170.33
[58] Field of Search .............. 356/410, 416, 417, 418, 356/419, 440; 250/573, 576; 73/170.33, 170.34

[56] References Cited

U.S. PATENT DOCUMENTS

| | | | |
|---|---|---|---|
| 3,773,424 | 11/1973 | Selgin | 250/576 |
| 3,861,809 | 1/1975 | Hall, Jr. | 356/418 |
| 3,910,701 | 10/1975 | Henderson et al. | 356/73 X |
| 4,043,668 | 8/1977 | Goetz et al. | 356/73 |
| 4,072,424 | 2/1978 | McMullan | 356/208 |
| 4,432,649 | 2/1984 | Krause | 356/438 |
| 4,673,819 | 6/1987 | Rose | 250/573 |
| 4,708,475 | 11/1987 | Watson | 356/417 |
| 4,804,849 | 2/1989 | Booth et al. | 250/459.1 |
| 4,986,665 | 1/1991 | Yamanishi et al. | 356/402 |

FOREIGN PATENT DOCUMENTS

| | | |
|---|---|---|
| 64-49941 | 2/1989 | Japan . |
| 842511 | 6/1981 | U.S.S.R. . |
| 1455296A1 | 1/1989 | U.S.S.R. . |

Primary Examiner—Robert J. Warden
Assistant Examiner—Christopher Y. Kim
Attorney, Agent, or Firm—Klarquist Sparkman Campbell Leigh & Whinston

[57] ABSTRACT

An absorption meter determines concentration of chlorophyll a and pheophytin in liquids. Particularly, an immersible absorption meter has a light source, a reflective flow tube, a signal detector, and means for determining the difference between the absorption coefficients at a first wavelength and a second wavelength. The light source may further include a plurality of filters and a selector that selects the filters. The concentration of substances in liquids is determined by measuring the absorption of light at a first wavelength and at a second wavelength, determining the difference between the absorption coefficients for the first and second wavelengths, and converting this data into concentrations.

20 Claims, 9 Drawing Sheets

IN SITU CHLOROPHYL ABSORPTION METER

GOVERNMENT SUPPORT

This invention was developed in part using funds supplied by the National Science Foundation, grant number NSF OCE 89-113355. The United States government may have certain rights in the invention.

This application is a continuation of application Ser. No. 07/918,529, filed on Jul. 21, 1992 now abandoned.

FIELD OF THE INVENTION

This invention is directed to a method and device for determining the light absorption of a material in a liquid.

BACKGROUND OF THE INVENTION

Absorption meters have long been used to measure the light absorption of materials. Prior absorption meters are sophisticated electronic devices that are sensitive to transportation and environmental perturbations. As a result, such meters are not capable of performing in situ analyses of liquids at remote sites. To analyze liquids in situ such as naturally occurring bodies of water, an absorption meter must be (1) transportable, (2) protected from liquid immersion, (3) protected from the extreme pressures that occur with increased immersion depth, (4) operational over wide temperature variations, and (5) fortified for on-board deployment. Prior absorption meters are not capable of withstanding the effects of immersion in natural bodies of water.

Furthermore, natural bodies of water are analyzed by collecting and transporting samples to a location more convenient for analyzing the sample. Transporting samples may result in their contamination or alteration. For instance, liquid samples are often concentrated on filters. Filtration techniques introduce errors not only through the process of sample handling and filtration, but also due to the optical effects of discreetness.

A second example of perturbations associated with removing samples to a remote site involves the collection of phytoplankton for chlorophyll concentration determinations. Phytoplankton samples are collected at various ocean depths in sample vials that are then brought to the ocean surface. Such phytoplankton experience rapid depressurization and exposure to light. Both depressurization and light exposure affect phytoplankton physiology, which can affect the amount of chlorophyll detected from such phytoplankton. For instance, exposing chlorophyll a to fluorescent light can degrade the chlorophyll a to pheophytin in a matter of minutes. Pheophytin has an absorption that is roughly three times lower than that of chlorophyll a. Hence, collecting and transporting phytoplankton samples alters the amount of chlorophyll that is measured at the remote site compared to the true amount that would be measured in situ.

Moreover, analyzing samples at a remote location does not provide an accurate depiction of a dynamic liquid in real time. For biological inquiries, real time monitoring of a dynamic system is particularly important.

At present, the only viable instrument for in situ chlorophyll concentration measurements is the fluorometer. For instance, Soviet Union Patent No. 842511 describes a submersible fluorometer useful for measuring chlorophyll concentrations. Fluorescent measurements of chlorophyll are less reliable than absorption measurements mainly because fluorescence is a two-step process: (1) chlorophyll receives light energy at a first wavelength; and (2) chlorophyll emits light energy at a second wavelength. As a result, fluorescence depends on the quanta absorption rate per chlorophyll a concentration and the quanta emission per quanta absorption rate. Both of these factors vary as a function of light and nutrient conditions, and fluorescence efficiency may therefore vary as much as a factor of ten.

Fluorometers also have a large sampling time constant that is on the order of about three seconds, which means that a fluorometer must sample for about three seconds in order to achieve adequate resolution. At short time constants the resolution of fluorometers is only about 0.1 $\mu g/l$. Also, fluorometers typically measure very low light levels, and use a flash lamp that has a large pulse-to-pulse instability. Hence, to get a precise measurement, a fluorometer must average over many-flash pulses. These two factors result in a large time sampling constant for fluorometers.

Moreover, phytoplankton with a set amount of chlorophyll will absorb a certain amount of light. However, the same phytoplankton's fluorescence depends on its physiological state, and the nutrient level.

Absorption has been used previously to determine the concentration of a wide variety of substances in a liquid. This method comprises preparing-known concentrations of a subject material and thereafter measuring the absorption of the material at a particular wavelength. This method is highly dependant upon obtaining accurate absorption data. For laboratory settings, external factors such as salinity and temperature can be stringently controlled. However, for in situ measurements, and especially for depth profile measurements of liquid bodies such as lakes and oceans, external conditions can not be as stringently controlled.

Chlorophyll concentration has been measured in the laboratory by determining the absorption of a liquid sample at about 675 nanometers (chlorophyll a has a strong absorbance band at approximately 675 nanometers) and at about 750 nanometers. The absorption at 750 nanometers is then subtracted from the absorption value at 675 nanometers to provide an absorption for chlorophyll a and pheophytin. We recently determined that the absorption coefficient is highly temperature dependent at about 750 nanometers. Hence, prior techniques that subtract the 750-nanometer absorption to determine the concentration of chlorophyll a introduce significant temperature-dependant absorption errors. Because chlorophyll a concentration measurements have typically been done at remote laboratory settings, it was not heretofore appreciated that in situ measurements (wherein the temperature is in constant flux), if an in situ absorbance meter had been available, would provide inaccurate chlorophyll a concentration data.

Light scattering is another problem encountered with differential absorption techniques for determining concentrations of particulate and dissolved substances. This problem has not been satisfactorily addressed by prior methods and devices used for concentrations involving differential absorption techniques. Light scattering can introduce significant error into absorption values, which in turn introduces error into the concentration values determined from this absorption data.

SUMMARY OF THE INVENTION

The present invention provides a method for measuring the concentration of a substance in a liquid comprising: (1) transmitting through a liquid sample light at a first wavelength of about 675 nanometers; (2) measuring the light transmitted through the liquid sample at 675 nanometers; (3) transmitting light through the liquid at a second wavelength of from about 710 to about 725 nanometers, and preferably 712 nanometers; (4) measuring the light transmitted through the liquid sample at from about 710 to about 725 nanometers (preferably 712 nanometers); (5) measuring a difference value between light absorbed by the liquid sample at the first and second wavelengths; (6) calculating an absorption coefficient from an amount of light transmitted at the two wavelengths; and (7) determining the concentration of the material in the liquid from the absorption data.

More particularly, the method of the present invention is directed to a method of determining the concentration of substance in a liquid, such as water, comprising: (1) immersing a liquid-tight absorption meter into a liquid, wherein the meter is protected from immersion in the liquid by a pressure case; (2) transmitting light at a first wavelength through the sample; (3) detecting light at the first wavelength after it is transmitted through the liquid; (4) transmitting light at a second wavelength through the sample; (5) detecting light at the second wavelength after it is transmitted through the liquid; (6) calculating an absorption coefficient from an amount of light transmitted at the two wavelengths; and (7) determining the difference between light absorbed by the sample at the first and second wavelengths and converting this difference into concentration data.

The present invention also provides a device for practicing the method discussed above. The device comprises an absorption meter for measuring the absorbance of a liquid in situ, the device having a pressure case, a light source located proximate the pressure case, filters for transmitting a selected wavelength of light through a liquid sample receiver, and a light detector adjacent the sample receiver for detecting light passing through a liquid sample located in the receiver. The device may further comprise a plurality of optical filters and a filter selector that selects filters from the plurality of filters in a determinable order.

In a preferred embodiment, the present invention provides a device for determining the concentration of chlorophyll in a liquid wherein the device comprises: (1) a pressure case; (2) a light source located proximate the pressure case; (3) a filter wheel located between the light source and a collimator, the filter wheel including a plurality of filters for transmitting a wavelength of light to the collimator by filtering light emitted by the light source; (4) a beam splitter to split light from the collimator into a plurality of beams, the collimator being located between the filter wheel and the beam splitter; (5) a reference detector placed to detect a reference beam from the beam splitter; (6) a sample receiver having a water inlet port and a water outlet port; (7) a reflecting tube located inside the sample receiver, the tube defining a channel of known pathlength for receiving water from the inlet port, the tube having inner walls that reflect an absorption signal; (8) a signal detector for detecting the absorption signal; (9) a signal amplifier connected to the signal detector; and (10) telemetrying means for sending and receiving an amplified signal from the signal detector.

The method and device described above solve the problems associated with prior spectrophotometers and methods for determining the concentration of chlorophyll in a liquid body. For instance, the present invention's preferred second-wavelength is at 712 nanometers rather than at 750 nanometers. The absorption at 712 nanometers is temperature independent, whereas the absorption at 750 nanometers is highly temperature dependent. The data obtained using the present device is also superior to the data obtained using prior devices and methods because: (1) errors introduced by light scattering have been reduced by moving the second wavelength from 750 to 712 nanometers; (2) the present device is based on chlorophyll absorption, as opposed to fluorescence, and therefore the variance associated with chlorophyll fluorescence is eliminated; (3) the present meter is liquid submersible; (4) the absorption meter achieves rapid sampling at higher resolutions than a fluorometer; (5) the absorption meters of the present invention utilize a sample chamber that is continuously exchanging the liquid sample; and (6) absorption correlates directly to chlorophyll concentration whereas fluorescence does not. Hence, the device is highly suitable for in situ real-time analyses of liquid bodies such as the ocean.

DETAILED DESCRIPTION OF THE INVENTION

Determining Concentration Using Absorbance Value Differences

Figure 1:
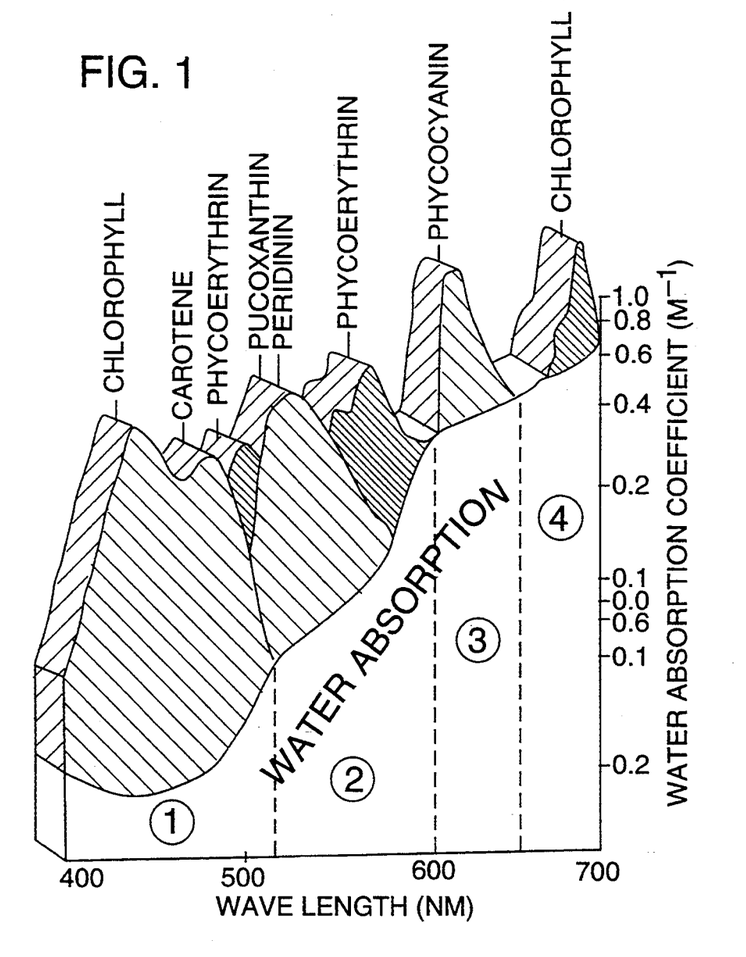
FIG. 1 is a graph for various algal pigments in naturally occurring water.

FIG. 1 is an absorption spectra of various algal pigments versus wavelength that clearly shows an absorption peak at approximately 676 nanometers (nm) for chlorophyll. Although many substances absorb in the 400–600 nm range, the 675 nm absorption peak is primarily due to chlorophyll a plus pheophytin (a porphyrin identical to chlorophyll a except that it lacks magnesium). An absorption spectra for chlorophyll a peak plus pheophytin provides useful information to oceanographers and limnologists. For instance, the concentration of chlorophyll a can be determined from its absorption.

The absorption for chlorophyll a plus pheophytin can be determined by measuring an absorption at about 676 nm and subtracting from this absorption an absorption at a second wavelength. The absorption at the second wavelength is subtracted from the absorption at 676 nm for two primary purposes: (1) to remove the effects of light scattering; and (2) to account for absorptions by non-chlorophyll substances, such as yellow matter. Both scattered light and absorbed light are typically measured by an absorption meter.. For purposes of the present invention, absorbed light is of primary interest. Hence, the absorption at the second wavelength is subtracted to obtain a true chlorophyll a plus pheophytin absorption without simultaneously measuring scattered light.

Non-chlorophyll absorptions must also be subtracted from the absorption at 676 nm to obtain an accurate chlorophyll a plus pheophytin absorption. In turn, the chlorophyll a plus pheophytin absorption provides information concerning the status of the ocean's primary producers. Hence, by subtracting the absorption at the second wavelength from the absorption at 676 nm, the effects associated with light scattering and absorption by non-chlorophyll substances can be eliminated.

Hence, an absorption for chlorophyll a plus pheophytin can be determined using a differential absorption method according to the method described above, if accurate absorption data is obtained. Variations in liquid temperature and salinity can affect measured light properties. For instance, changes in the absorption coefficient alter measured light properties such as irradiance and reflectance. Temperature affects the absorption coefficient of water at the O—H bond-stretching harmonics in an absorbance spectra, whereas the effects of salinity on the O—H bond are manifested in reflectance and Raman scattering, and on the absorption of water in the near-infrared. The influence of temperature and salinity on the absorption of water in the harmonics regions are related to formation of tetrahedral hydrogen-bonded water macromolecules. Increasing temperature and salinity break up the hydrogen-bonded water macromolecules. Changes in the proportion of water macromolecules with variations of temperature or salinity are seen as changes in the absorption of water at harmonics of the O—H bond stretching frequency.

There is a need for an absorption meter for measuring natural bodies of water in situ. To provide the best possible absorption data, environmental effects on absorption, such as temperature and salinity, were investigated using a dual-beam Cary 118 spectrophotometer. The spectrophotometer measured transmittance in 1 nm intervals between 800 and 700 nm and in 5 nm intervals from 700 to 405 nm. Samples were placed in one beam and the reference path was left empty.

Clean fresh water was obtained using a reverse osmosis filter. Samples of 400 ml were placed in a covered beaker in a temperature controlled bath. A ten cm quartz cuvette was then filled with sample water and analyzed using the spectrophotometer.

A salt water sample with a salinity of approximately 29 psu was prepared using an aquarium salt mix. The artificial sea water sample was passed through a 0.3 μm Nuclepore filter before being placed in the sample cuvette.

Temperature measurements were made before and after each scan to determine the temperature drift during the sampling period. The spectrophotometer took one minute to scan the 800–700 nm range and another 1.25 minutes to scan the 700–400 nm range. The temperatures listed on all figures are ±0.5° C. for measurements at 21° C. and ±1.0° C. for every ten degrees above or below 21° C.

To ensure that changes in absorption measured were not due to changes in the absorption of the sample cuvette, absorption measurements were made of the empty quartz cuvette at room temperature and again after the cuvette had been in a freezer for two hours. The cuvette's absorption coefficient did not display a temperature dependence.

The results of this and previous work indicate that absorption at 685 nm is invariant with changes in temperature. Hence, all curves were adjusted to the absorption value at 685 nm, to allow changes in the shape of the curves to be easily studied. Since there was no evidence that the quartz cuvette was responsible for changes in measured absorption the changes must be due to changes in the absorption coefficient or index of refraction of water.

Figure 2:
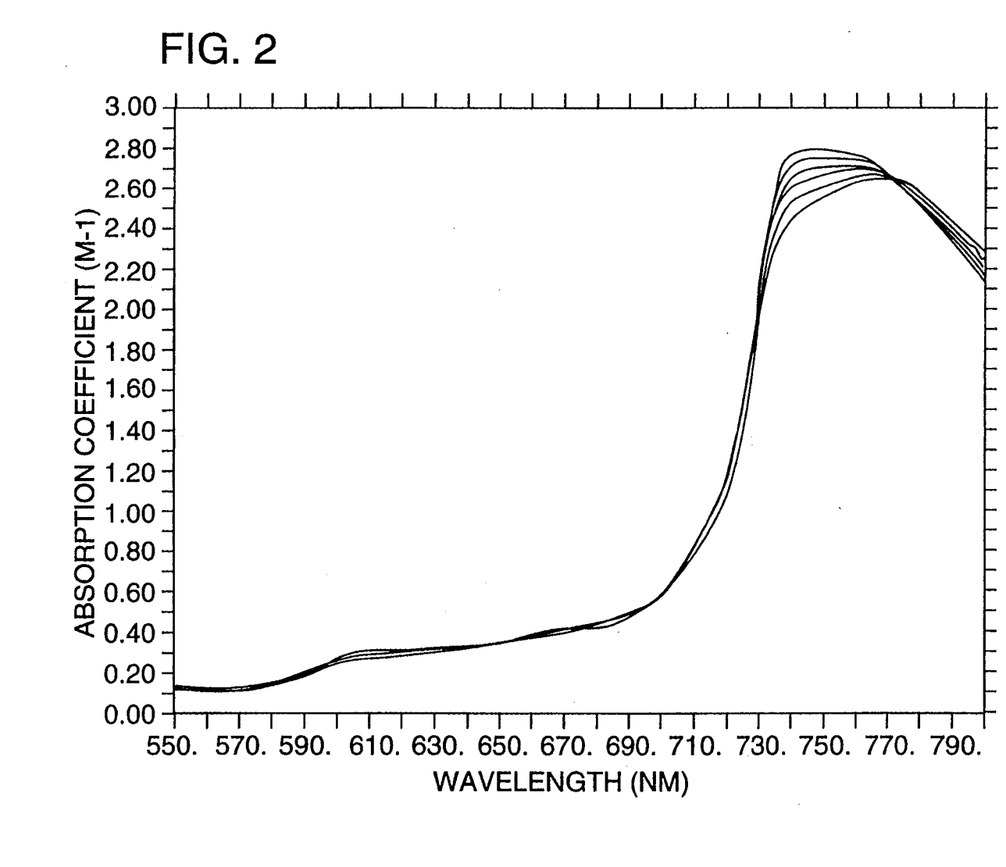
FIG. 2 is graph of absorption coefficient versus wavelength.

Some of the results from these studies are presented in FIG. 2, which is a graph of the absorption coefficient in inverse meters versus wavelength. Although there is slight variation in the graph between from about 550 nm to about 690 nm, this region of the graph is relatively linear, and thus invariant. However, the graph between about 720 nm and 750 nm clearly shows the effect of temperature on absorption. Hence, if 750 nm absorption is used as the second wavelength, significant errors may be introduced into obtaining an absorption for chlorophyll a plus pheophytin. Hence, using the 750 nm absorption to remove light and absorption for non-chlorophyll materials for measuring natural bodies of water in situ introduce significant error into the determination of chlorophyll a plus pheophytin concentration. The absorption maximum shifts towards 745 nm with increasing temperature, and there appears to be a crossover region at approximately 775 nm where there is little or no temperature effect. At wavelengths between 775 and 800 nm an increase in temperature causes a decrease in absorption. At 750 nm an increase is shown in the absorption coefficient of approximately 0.25 m$^{-1}$ for a 25° C. temperature shift within the range of 0° to 30° C., which is the range of oceanographic interest. At a given wavelength the change in the absorption coefficient with temperature is linear. The magnitude of the slope of the linear regression changes with wavelength which represents the shift in the absorption peak. Linear regression data for 745, 750, and 755 nm is given in Table 1.

TABLE 1

| wavelength | slope | S.D. of slope | r2 |
|---|---|---|---|
| 745 nm | 0.0113 | 0.0003 | 0.996 |
| 750 | 0.0092 | 0.0003 | 0.993 |
| 755 | 0.0071 | 0.0002 | 0.996 |

Using the value of the absorption coefficient for 750 nm given by Smith and Baker (1981) a change in temperature of one degree changes the absorption coefficient by 0.4 percent (with $\Delta a(750)/\Delta T \approx 0.01$ m$^{-}$°C.$^{-1}$).

As a result of this study, it was determined that the 750 nm baseline absorption peak cannot be used to produce accurate data in situ. However, FIG. 2 also shows that the region from about 700 nm to about 725 nm is relatively temperature insensitive. Hence, an absorption in this region can be used to subtract the effects of scattering and non-chlorophyll absorptions from the 676 nm absorption, which allows the differential absorption technique to be used for analyzing natural bodies of water in situ.

Using a second absorption of from about 700 nm to about 725 nm is superior to previous approaches for another reason. The effects of light scattering on absorption are generally proportional to $\lambda_2/\lambda_1$, although this relationship is dependant upon the nature of the substance in question. By decreasing this ratio, the effects of scattering are also reduced. More specifically, changing the second wavelength ($\lambda_2$) from 750 nm to from about 700 nm to about 725 nm minimizes the effects of scattering on absorption data, and the light scattering errors more easily corrected. And, the closer $\lambda_2$ is to 676 nm within the range of from about 700 nm to about 725 nm, without infringing upon the chlorophyll peak itself, the less light scattering interferes with the chlorophyll absorption.

Optical filters can be used to selectively transmit light of a particular wavelength. Filters have a certain band width associated therewith. For instance, filters used with the absorption meter described below have a half-maximum peak band width of about 10 nm. A filter having a maximum transmittance at about 715 nm will have a light transmittance of from about 710 nm to about 720 nm. Optical filters can be obtained that have a smaller band width; however, these filters also decrease the light through-put. Hence, a particularly suitable second wavelength absorption useful for the present invention is centered about 712 nm for filters having a band width of about 10 nm.

Chlorophyll a and pheophytin have a standard absorption value of from about 0.015 to about 0.02 $m^{-1}/\mu gl^{-1}$, although this value may vary from location to location. The apparatus according to the present invention can provide raw absorption data for chlorophyll. Alternatively, the absorption coefficient for chlorophyll, which can be determined at an accuracy better than about 0.0005 $m^{-1}$ with an absorption meter according to the present invention, can be multiplied times the standard adsorption value to determine the chlorophyll concentration. Because the standard chlorophyll absorption varies from location to location, this standard value is best determined empirically for each location of interest. The empirically derived value can then be used repeatedly to determine chlorophyll concentration at that location.

Absorption Meter

Based on the foregoing, we have developed an absorption meter for measuring the absorbance of materials in a liquid. A preferred embodiment of the meter is used to determine the concentration of chlorophyll a plus pheophytin, either as particulates or dissolved in an aqueous medium. One skilled in the art will realize that the method can be extended to analysis of materials other than chlorophyll if (1) temperature and other environmental effects are accounted for, and (2) a representative absorption peak is known for the substance of interest. The chlorophyll meter of the present invention is useful for in situ analyses of liquids such as ocean water and lake water. In general, the chlorophyll meter includes a liquid-tight pressure case, light means, signal detector, and a sample receiver having a sample inlet and a sample outlet for continuously receiving a liquid sample in situ.

A particularly suitable embodiment of the present invention includes a pressure case, a light source located proximate the pressure case, and a filter wheel for selecting a particular wavelength of light wherein the filter wheel typically includes a plurality of filters. A filter wheel particularly suitable for a chlorophyll meter includes a filter that transmits light having a wavelength of 675 nanometers, and a second filter that transmits light having wavelengths from about 710 nm to about 725 nm. This second filter was chosen as a result of our recent investigations concerning environmental effects on absorption spectra. Light is transmitted through these filters and then guided down a reflecting tube located inside a sample chamber. This reflecting tube reflects a substantial portion of the scattered light transmitted through the filter and through the liquid sample occupying the sample chamber.

Figure 3:
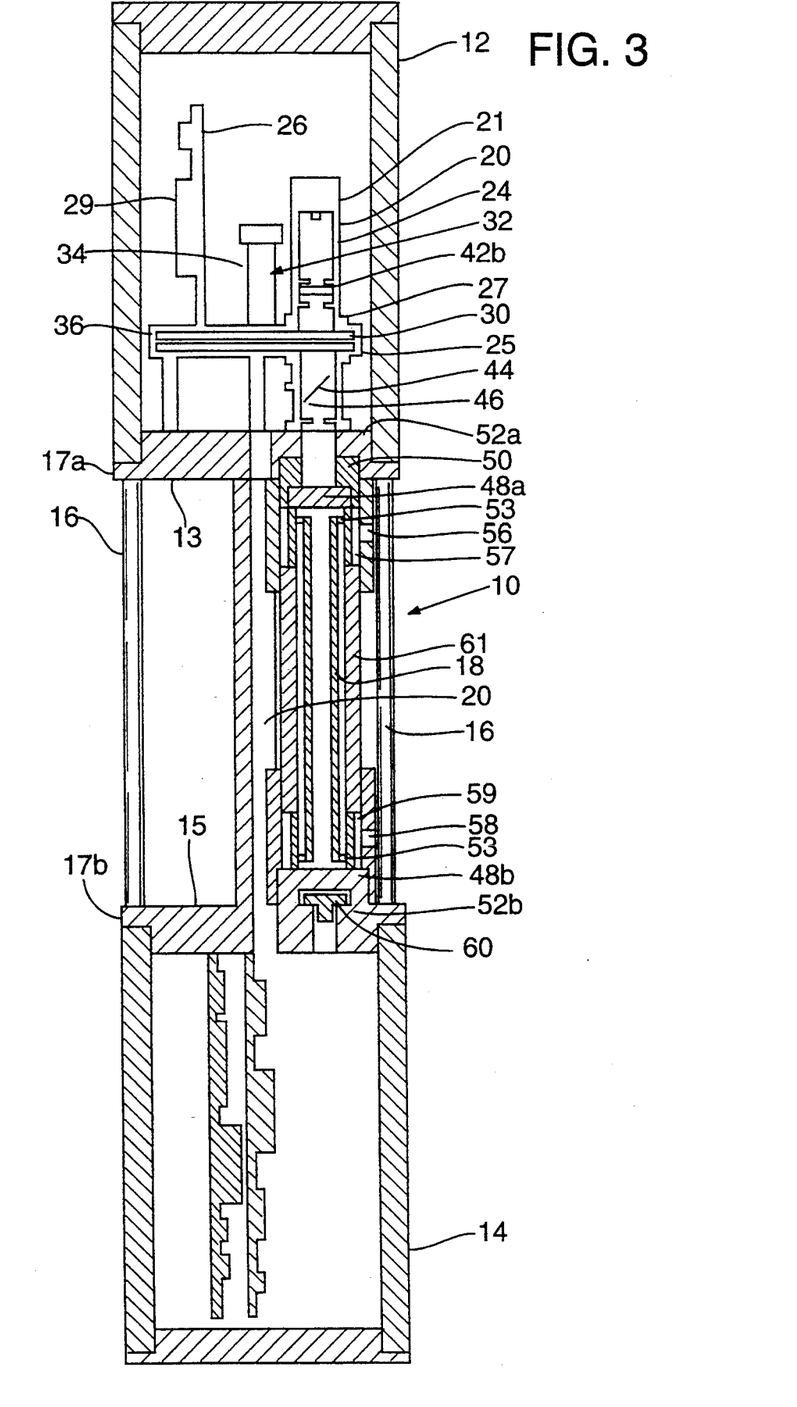
FIG. 3 is a schematic drawing of an absorption meter according to the present invention.

With reference to FIG. 3, a particularly suitable embodiment of a chlorophyll meter 10 will now be described. The chlorophyll meter comprises a first pressure case 12, and a second pressure case 14. Pressure cases 12, 14 flank a middle region that is open to liquids. The middle region includes a reflective flow tube 18 and a fluid-tight tube that defines an electronics feed-through channel or passageway 20. Pressure cases 12, 14 are joined by three steel rods 16 that are situated at relative angles of 120 degrees from the vertical axis and that pass into pressure flanges 17a, 17b of pressure cases 12 and 14 respectively.

The chlorophyll meter 10 is a sensitive electronic device. Hence, to provide an immersible chlorophyll absorption meter, the device must be protected from immersion in a liquid and pressures associated with increasing liquid immersion depth. One embodiment of the absorption meter comprises pressure cases 12, 14 made of polyvinylchloride (PVC), Delrin, or polycarbonate polymers. PVC and polycarbonate polymers are preferred materials for pressure cases intended for use at immersion depths of 100 meters or less. Polycarbonate polymers can be obtained from a number of companies such as Laird Plastics of Portland, Ore., U.S.A. These materials suffice if the meter is to be submersed in water only up to depths of approximately 500 meters. However, for an absorption meter to survive under the pressure exerted when immersed in a liquid to depths greater than 500 meters, and up to about 10,000 meters, a different material is used to construct the pressure case. Suitable materials for protecting the device from such higher pressures include titanium and stainless steel.

Pressure case 12 includes a light source 20 such as a lamp 21. A suitable light source 20 includes a tungsten lamp 21 which generates white light. A particularly suitable tungsten lamp is made by Carly Lamps of Los Angeles, Calif., U.S.A. One embodiment of a particularly suitable tungsten lamp is Carly Lamps, Model No. 259. Suitable Carly lamps for the chlorophyll meter are TL-1 evacuated lamps having a diameter of about 0.1 inch. Light source 20 is securely attached inside pressure case 12 using an aluminum housing made from an aluminum block machined to receive an anodized aluminum lamp sleeve 24. The lamp sleeve 24 is attached to a filter wheel housing 25. The aluminum lamp sleeve 24 is attached to the filter wheel housing 25 by any suitable means. A particular embodiment of the present invention attaches the lamp sleeve housing 24 to the filter wheel housing using three set screws (not shown) that penetrate through wheel housing flanges 27 and into the wheel housing 25. The aluminum housing is secured inside the pressure case using any suitable means known in the art. Lamp housing 24 is then secured to the aluminum housing, using any suitable means such as epoxy.

A regulated electrical lamp power supply 26 is also included in the pressure case 12. A particularly suitable lamp power supply 26 is built around a power operational amplifier 29, and a particularly suitable power operational amplifier 29 is made by Burr Brown, of Tucson, Ariz., part No. OP511.

The power op amp 29 provides regulated voltage to approximately 10 parts in a million. Approximately 5 volts and approximately 0.25 amp are required to power one embodiment of the tungsten light source 20, and the chlorophyll meter 10 requires 0.11 amp.

Figure 8:
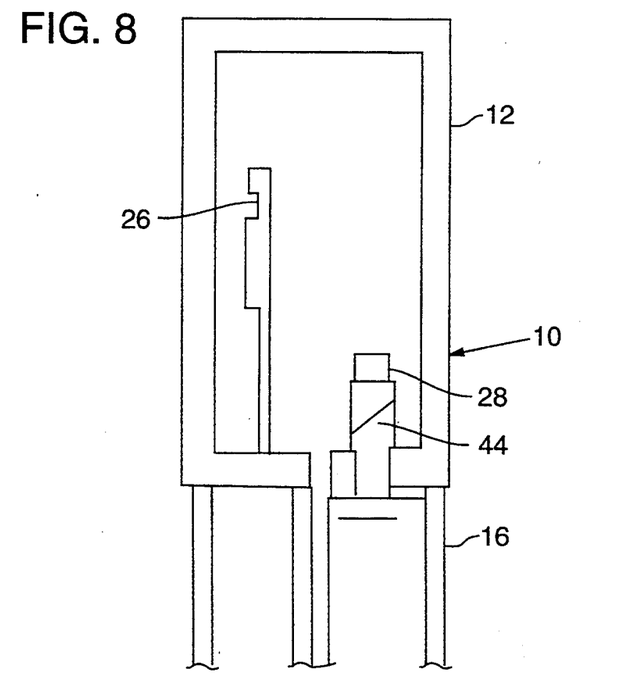
FIG. 8 is a schematic drawing of an alternative embodiment of an absorption meter according to the present invention.

An alternative embodiment of absorption meter 10 is shown schematically in FIG. 8. For this embodiment, light source 20 comprises light-emitting diodes (LEDs) 28 for generating light of particular wavelengths. Standard light-emitting diodes can be purchased and many companies will specifically design LEDS to emit light of given wavelengths. A chlorophyll meter according to the present invention can employ any light-emitting diode that is specifically designed to generate light at wavelengths of 675 and any that generates light from about 710 nm to about 725 nm.

Figure 4:
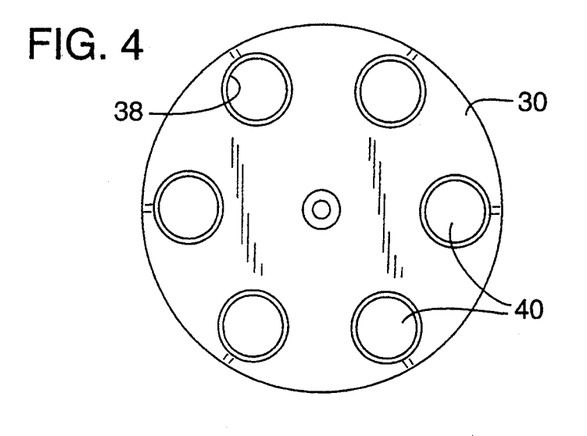
FIG. 4 is a schematic drawing of a filter wheel according to the present invention having a plurality of filters.

Referring again to FIG. 3, tungsten light source 21 emits white light. The white light must be filtered in order to select desired wavelengths. Hence, a filter wheel 30, shown in both FIG. 3 and FIG. 4, is included in the pressure case 12. The filter wheel 30 is described in further detail below. The position of the filter wheel 30 must be determinable so that separate filters, such as the 675 nm and 710 nm to 725 nm filters, can be aligned between the light source 20 and a sample receiver or sample chamber. A particularly suitable arrangement utilizes a rotatable filter wheel 30. The filter wheel rotation device comprises a motor/encoder 32 made by MicroMo of St. Petersburg, Fla., U.S.A. The motor/encoder 32 comprises both a motor 34 and an encoder 36, as the name implies. The encoder 36 measures the rotational position of the motor 34. The encoder 36 breaks a single rotation of the motor 34 into 500–512 successive steps. The purpose of the encoder 36 is to provide means whereby the motor 34 can accurately align filters 40 (not shown in FIG. 3) in the filter wheel 30. The encoder 36 operates at a nominal voltage of about 5 volts and provides information concerning the exact rotational location of the filter wheel 30.

A particularly suitable embodiment of the meter continually samples a liquid flowing through a reflective flow tube 18. In order to do this, the filter wheel 30 must be continuously rotated. The rotation speed of the motor 34 is controlled by controlling the voltage it receives. The voltage supply to the motor is controlled using a voltage regulator (not shown), part number LM317, made by several manufacturers, including National Semiconductor, Santa Clara, Calif., U.S.A., and Motorola. The voltage regulator can be adjusted simply by changing an external resistor to a reference voltage pin (not shown), thereby changing the voltage that is received by the filter wheel motor 34. One skilled in the art will realize that the rotation speed of the filter wheel 30 can be varied according to the purpose desired. A particular embodiment of the chlorophyll meter 10 rotates the filter wheel 30 at 20 Hz. Another embodiment of the present invention had a rotation speed of approximately 7 Hz. A 20 Hz rotation is more desirable because it increases the sampling rate, thereby allowing profiling of the water at a faster rate. Moreover, if a depth profile of the ocean is desired, approximately on 1 cm intervals, a sampling rate greater than 7 Hz is desired, and sampling rates as high as 100 Hz are within the scope of the present invention.

The filter wheel 30 also comprises filter housings 38 for housing a plurality of filters 40 (See FIG. 4). One embodiment of the present invention is capable of holding six filters. However, one skilled in the art will realize that the number of filters is not to be limited by this disclosure, but is rather a function of the purpose of the absorption meter 10. Specifically, for a meter that is to be used solely as a chlorophyll meter, only two filters are required, one filter transmitting light of approximately 675 nm, and the other filter transmitting light from about 710 nm to about 725 nm. Increasing the number of filters increases the accessible spectral band. By increasing the number of filters, more detailed spectral signatures of a liquid can be obtained.

The tungsten light source 21 also includes a lens (not shown) on the tip of the lamp. The lens focuses the light emitted by the lamp so that the light has a particular beam spread angle. Situated between the lamp lens and the filter wheel 30 is an achromat lens 42. The effect of this achromat lens 42 is to collimate the light incident thereon. A 50 mm achromat lens 42a has been used in previous embodiments of the present invention. However, a 30 mm achromat lens 42b can be used to make the chlorophyll meter 10, thus achieving better light throughput than 50 mm achromat lens 42a.

After the light is filtered by passing through a filter 40 housed on the filter wheel 30, it is then split into a plurality of beams by a beam splitter 44. A suitable beam splitter 44 comprises a thin, glass window, situated at an acute angle, such as about 45°, relative to the longitudinal axis of the reflective flow tube 18. The beam splitter 44 reflects approximately 10 percent of the light 44 incident thereon at an angle relative to the axis of the reflective flow tube 18. This reflected beam is referred to as a reference beam. The reference beam is thereafter detected by a reference signal detector 46. The reference signal compensates for drift in the light source 20. As the light source 20 ages, or as the chlorophyll meter 10 warms up, there are slight variations in the lamp output even though the voltage to the light source 20 is regulated. By measuring the ratio of the reference beam to a signal beam passing through the beam splitter 44, the output of the lamp 21 can be adjusted to compensate for lamp-output changes. A particularly suitable reference detector is made by United Detector Technology, of Los Angeles, Calif., U.S.A. A preferred embodiment of the reference detector is Model Number UDT555.

The two pressure cases 12, 14 also include pressure windows 48 that extend through one face 13, 15 of each pressure case 12, 14, respectively. Pressure windows 48 enable light to be transmitted from the light source 20 located in the pressure case 12 through the reflective flow tube 18, and into the second pressure case 14. Pressure windows 48 transmit light in the visible region. One embodiment of the pressure windows 48 can be made from acrylic. However, for increased strength, a particularly suitable pressure window 48 can be made from a polycarbonate polymer or quartz. Quartz suitable for pressure windows 48 of the present invention can be obtained from Heraus Amersill, of Atlanta, Ga., U.S.A. Pressure windows 48a, 48b are placed in openings in the faces 13 and 15 of the two pressure cases 12, 14 respectively, and are held in place by pressure window holders 52a, 52b. The pressure windows are secured into the pressure window holders 52a, 52b using any suitable means such as by a PVC solvent cement.

Also connecting pressure cases 12, 14 is an electronics feed-through 20 that may be made of any suitable material, such as PVC, Delrin, polycarbonate polymer, or stainless steel. Electronics feed-through 20 defines a channel for housing electric wires. The electronics feed-through 20 is sealed to facing sides 13, 15 of the two pressure cases 12, 14, using piston O-rings (not shown). Electronics feed-through 20 defines a channel that equalizes the pressure between pressure cases 12, 14.

A reflective flow tube 18 is designed to be at the same pressure as the pressure external to the meter 10. The reflective flow tube 18 includes attachment sleeves 50 that are telescopic in nature, and that engage pressure window holders 52 affixed to each of the pressure cases 12, 14. Pressure window holders 52 define channels for receiving pressure windows 48a and 48b, thereby allowing the transmission of light from light source 20 through flow tube 18 and into pressure case 14. By slipping the flow tube attachment sleeves 50 over the pressure window holders 52, the flow tube 18 is thereby inserted and aligned with the rest of the meter's 10 optical path. The flow tube 18 is held inside the flow tube attachment sleeves 50 using O-rings 53. The telescopic nature of the attachment sleeves 50 allows reflective tube 18 to be inserted and detached readily for such purposes as cleaning or replacement.

Reflective flow tube 18 includes a sample inlet 56 and a sample outlet 58. The sample inlet 56 leads to a sample inlet reservoir 57 that opens into the interior of the flow tube 18. Similarly, the sample outlet 58 includes a sample outlet reservoir 59. The inlet 56 receives a liquid sample that is channeled through the reflective tube 18 along its longitudinal axis. Hence, the reflective flow tube 18 acts as a sample receiver or sample chamber by receiving liquid from the sample inlet 56 port and having the liquid exit the sample outlet 58. The interior of the reflective tube 18 comprises a quartz sleeve that is isolated from the Delrin, PVC, polycarbonate, or stainless steel housing 61 so that there is an air space interface between quartz portion reflective flow tube 18 and the housing 61. This air space provides an internally reflecting flow tube. This arrangement creates internal reflection because the liquid is a region of high refractive index, and the air space has a lower index of refraction. If the liquid is water, the refractive index is about 1.3. The air space has an index of refraction of about 1.0. Light entering the reflective flow tube 18 is scattered and impinges upon the interior sides of the flow tube 18. Relative to the longitudinal axis of the flow tube 18, which has a typical axis length of approximately 10–25 centimeters, light scattered at less than an angle of approximately 41 degrees is reflected back into the water-flow pathway. Hence, there is a tube-air interface that acts as a reflecting device as a result of the difference in refractive indexes.

The reflective flow tube 18 defines a region for receiving a liquid sample, the region having a fixed pathlength. This pathlength may vary as one skilled in the art will appreciate. A particular embodiment of the present invention uses a flow tube 18 having a pathlength of approximately 25 cm. However, a chlorophyll meter 10 may have a smaller reflective tube 18. A suitable pathlength for the chlorophyll meter flow tube is approximately 10 cm. This decreased pathlength has several advantages. First, it decreases the size of the overall device. Second, the sampling rate is ultimately dependent upon the residence time of a sample within the reflective flow tube 18. By decreasing this residence time, the sampling rate can be increased. For a tube having 25 cm pathlength, the sample residence time is on the order of one second. However, by decreasing the pathlength of the flow tube 18, the electronic precision of the light measurement must also be increased. The electronic precision can be increased by obtaining filters having enhanced surface uniformity, i.e. decreasing the error in the absorption coefficient from 0.001 $m^{-1}$ to about 0.0001 $m^{-1}$. Such filters can be commercially purchased or specially made.

A liquid sample is pumped through the reflective flow tube 18. The pump rate can be adjusted to change the sample residence time. Presently, the chlorophyll meter 10 uses a standard pump (not shown), that is exterior to the absorption meter 10 to pump the liquid sample through the sample inlet 56 and thereafter down the longitudinal axis of the reflective flow tube 18. That pump can be purchased from Seabird Instruments of Seattle, Wash., U.S.A. The reflective flow tube can be sealed at both ends and used in bench-top applications as well as for in situ applications. When the meter 10 is used for bench-top applications, the pump may not be required.

Light of a particular wavelength is transmitted through a liquid sample housed in the reflective tube 18, and is then detected by a signal detector 60. The purpose of the signal detector 60 is to collect scattered and direct beam light, thereby measuring the absorption of material, such as chlorophyll a and pheophytin, that may be in the liquid. A particularly suitable signal detector 60 is Model Number UDT 25 DP, made by United Detector Technologies of Los Angeles, Calif., U.S.A.

The signals that are received by both the reference signal detector 46 and the signal detector 60 are transmitted to a preamplifier which is an analog current to voltage preamplifier. A particularly suitable preamplifier is made by Burr Brown of Tucson, Ariz., U.S.A., Model number OPA 177. After the signal is amplified, it is then sent to a programmable gain amplifier (PGA). A particularly suitable PGA is a Burr Brown Part Number PGA 100. The purpose of the PGA is to amplify signals from the preamp in a programmable fashion so as to create signals of approximately the same intensity and to optimize system dynamic range. Dynamic range is a function of minima quanta of measurement divided by the total possible signal. For instance, for a 5.0 volt signal that can be measured with a 1 millivolt precision, the dynamic range is one part in 50,000. For the present invention, a dynamic range on the order of about 100,000 is desirable. For a broad band spectrum light source, such as one that might generate a red and blue wavelength light, the output for the red and blue wavelengths may vary considerably. For instance, the output from such a source may vary in the red and blue output by as much as a factor of 15. The PGA amplifies the low output signal from the light source to account for these varying signal intensities. For the chlorophyll meter 10 there is no need for a PGA because the chlorophyll meter 10 uses two wavelengths that have relatively the same output values from the light source 21. However, one skilled in the art will realize that the present device can be adapted to detect the absorption of substances other than chlorophyll a and pheophytin. For such instruments, the PGA may be required.

The analog signal from the amplifier(s) is sampled by a Burr Brown A to D sampler, Model number ESP 102. This sampler is an eighteen bit digital signal processing unit that continuously samples at about 100 KHz. The purpose of this unit is to convert the analog signal to a digital signal, which is continuously sent to the controller unit. A particularly suitable controller unit is a Motorola Controller, Part Number 68HC16. The function of the controller is outlined in the flowchart of FIG. 5. This controller has a queued serial module interface for taking serial input, referred to as a QSM module, which is built into the chip. The controller determines a position from the encoder 36 at which to start reading the analog to digital signal. Once a position is found, the controller starts sampling its QSM interface for a given number of samples. For instance, the controller may sample its QSM interface as the light scans across a filter from about 50 to about 200 times, depending upon rotational speed of the filter wheel and software.

The light source 20 is continually emitting light. Hence, the absorption meter 10 samples during phases whereby light passes through the filter, and it also samples during times when an opaque region of the filter wheel is interspersed between the light source 20 and the reflective flow tube 18. Hence, the meter 10 is sampling during an "on" (light through a filter 40) and an "off" period (light blocked by an opaque region of the filter wheel 30). The controller determines the difference in the signal from the on period and off period. By sampling the on and off periods, instrument differences resulting from the temperature coefficients of the individual parts are eliminated. Furthermore, by sampling during an off period, and subtracting this from the on period, errors introduced by ambient light are eliminated.

The illustrated meters 10 oversamples, i.e. as light goes through a filter, the absorbance is not measured once, but rather a plurality of times, such as about 100 times. This is also true of the dark phase of the filter 40. The purpose of oversampling is to improve the signal to noise ratio. If a sample measurement is taken only once, only about fourteen bits of resolution are obtained. By sampling 100 times, this resolution is increased to about sixteen to eighteen bits. Oversampling also allows the meter 10 to compensate for improper filter alignment. By integrating over the filter area, position errors and surface imperfections in the filters 40 can be eliminated.

Figure 5:
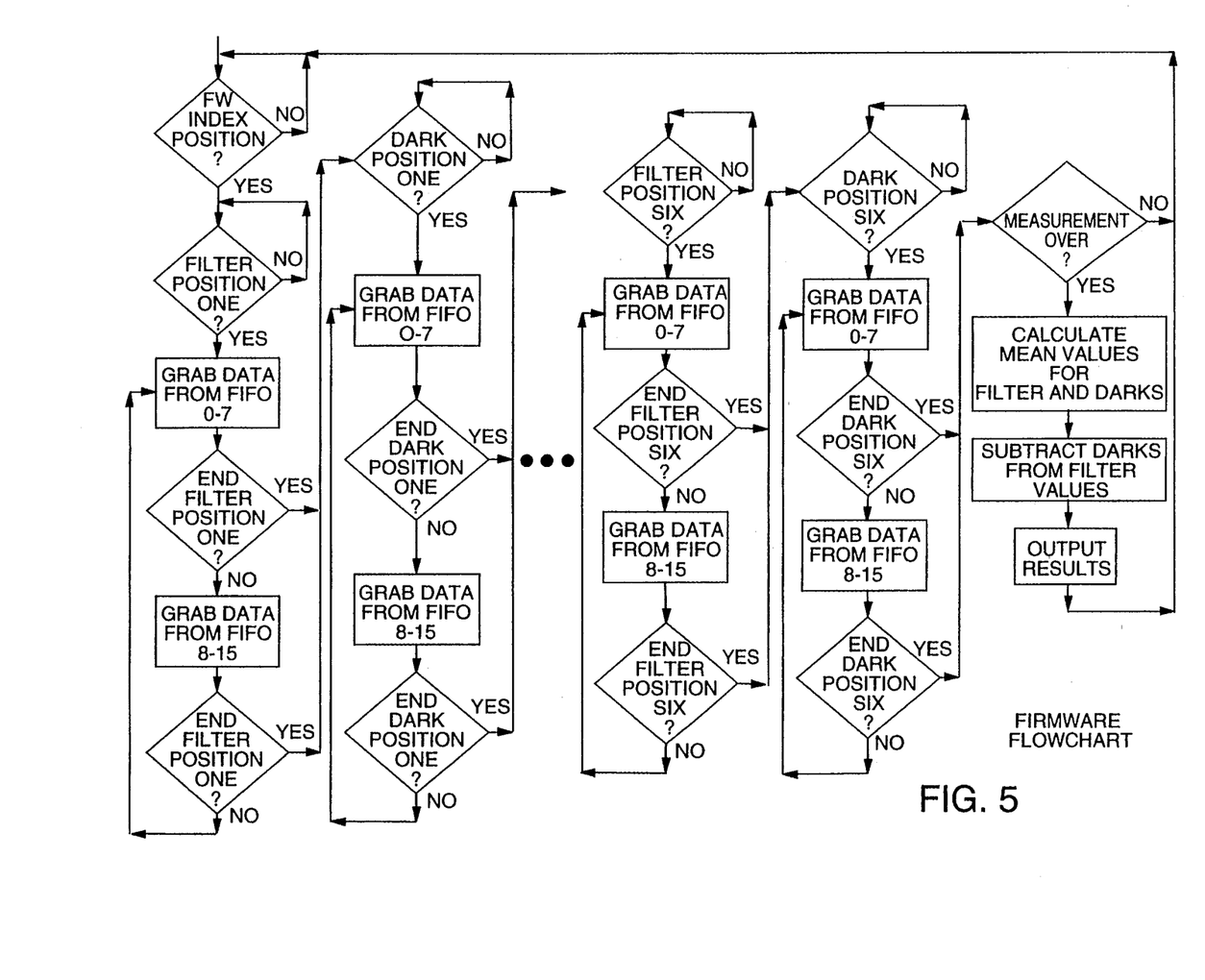
FIG. 5 is a firmware flowchart for an absorption meter according to the present invention.
Figure 6:
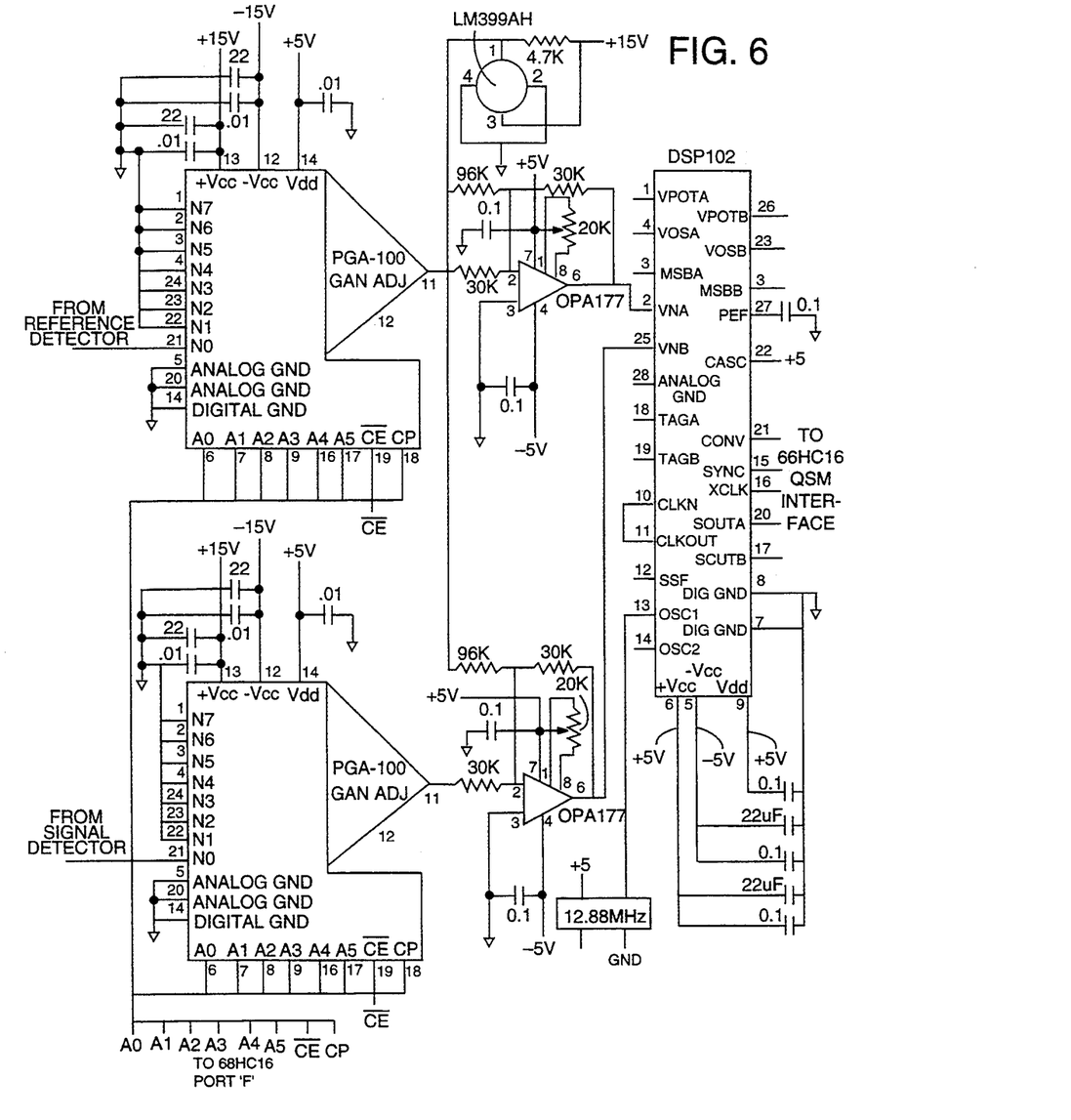
FIG. 6 is an electrical schematic for a programmable gain amp for use with the absorption meter according to the present invention.
Figure 7:
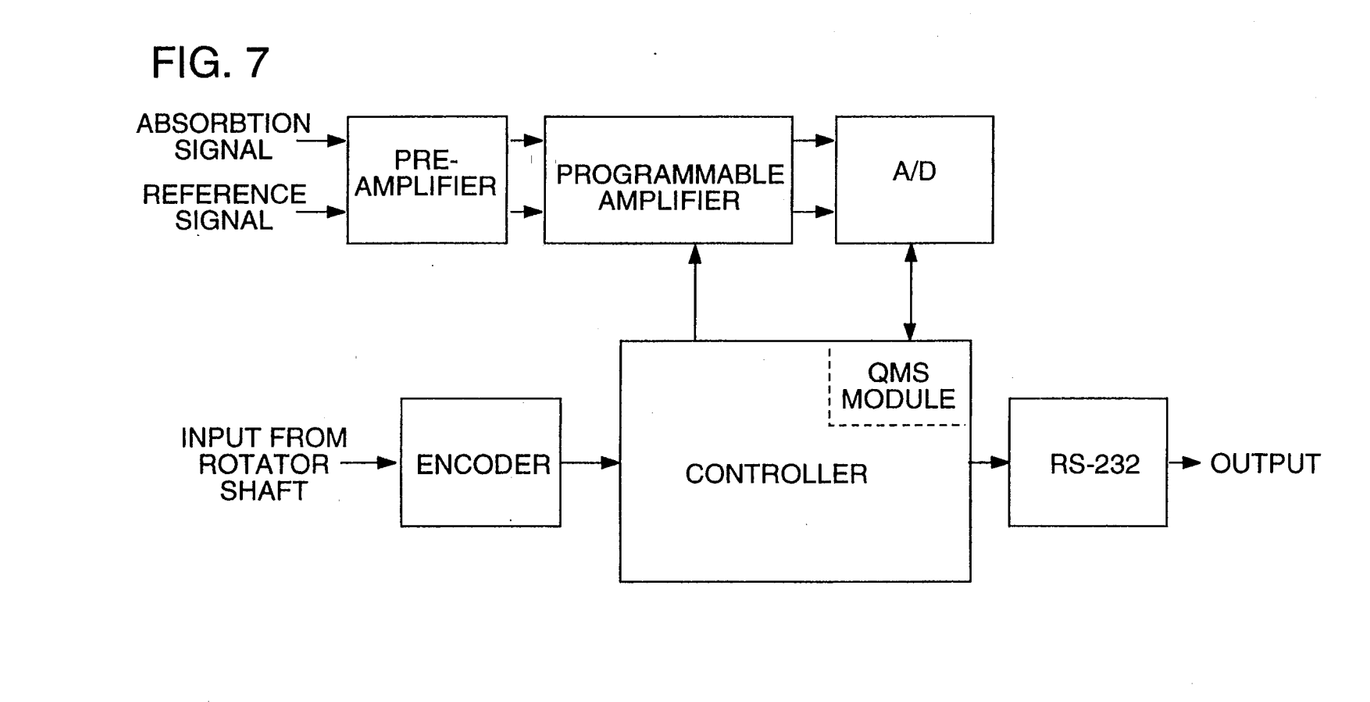
FIG. 7 is an electronics block diagram for an absorption meter according to the present invention.

The data from the QSM (both the reference signal and the absorption signal) are sent to a processor (see FIG. 5). The processor samples over a dark period and samples over a light period, and sums the sample measurement for a particular dark or light period. The processor then takes the difference between the value for a summed dark period and a summed light period, both for a light period at the 675 wavelength and the 710 nm to about 725 nm wavelength. The actual values for each period are then telemetried to a remote site, such as a ship on the surface of an ocean, using, for example, an RS 232 interface or an RS 485 interface.

At the remote receiving station, a difference between the absorption coefficient derived from 675 and 712 is computed. This provides an absorption valve for chlorophyll a plus pheophytin. This absorption value can then be converted into a chlorophyll a plus pheophytin concentration. In the chlorophyll meter 10 this calculation may be done by an HC16 microprocessor, or at the remote receiving station.

To use the absorption meter 10, it is either lowered by a cable directly into the water or placed on a conductivity temperature depth sensor (CTD). Absorption meters according to the present invention can be made to include a depth gauge. Such depth gauges typically measure depth by sensing the change in pressures associated with increasing immersion depth. Absorption meters according to the present invention have two modes of recording. First, the meter can record internally and save the obtained data. Then, when the device is returned to the surface of a body of water, the data in memory can be retrieved. The raw data for the present invention is the detected voltages at the 676 nm wavelengths and the voltage detected at the 700-725 nm wavelength. These voltages are then converted into absorptions by the central processing unit. Second, the device can be used to actually provide the chlorophyll concentration by adding a microprocessor that calculates the chlorophyll concentration directly. The calculation used to convert voltages to absorptions is: $-4 \log(V_1) - (-4 \log(V_2)) +$ scattering correction factor (nominally $\lambda_2/\lambda_1$) + calibration factor (empirically derived). The value obtained form this calculation is proportional to the chlorophyll concentration wherein the proportionality constant is about 0.015 $m^{-1}/\mu gl^{-1}$. This proportionality constant is determined empirically.

Figure 9:
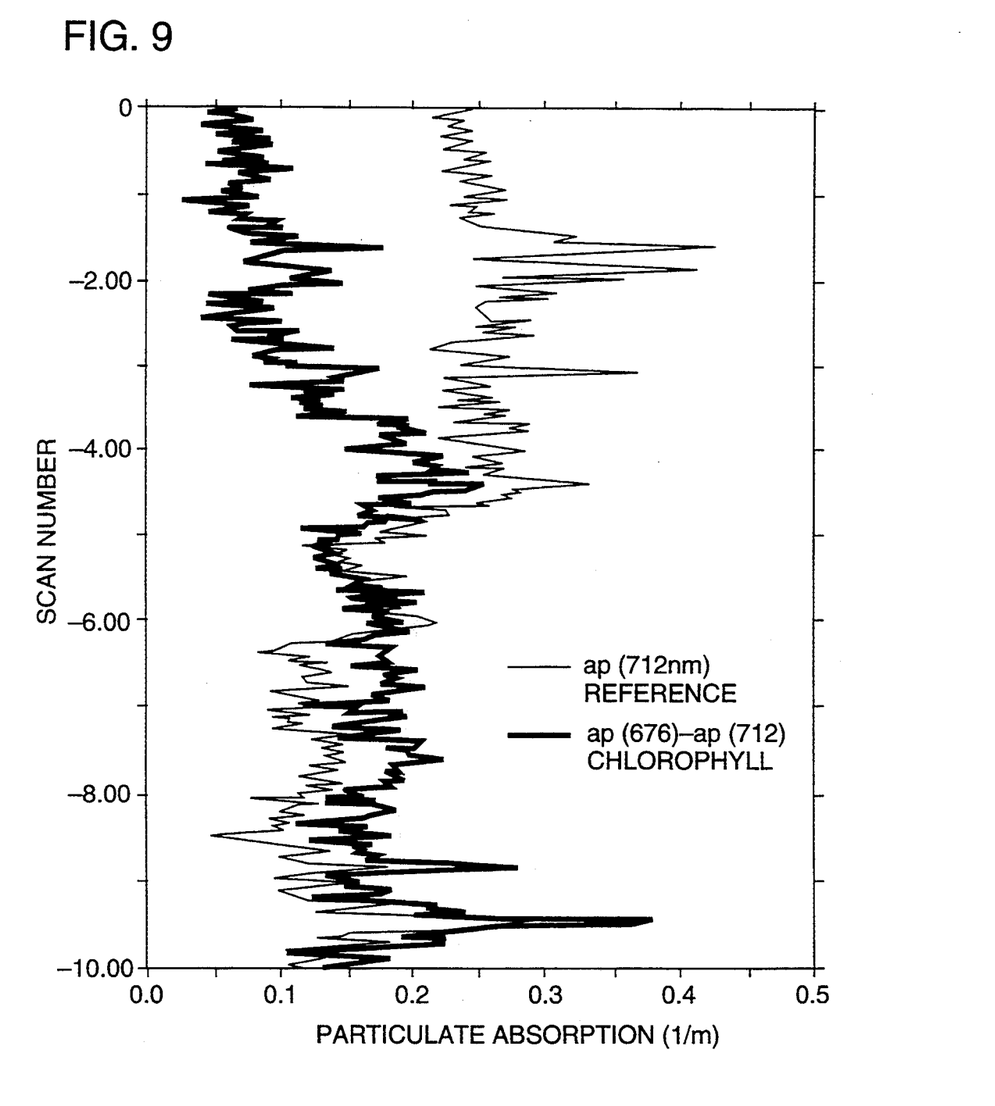
FIG. 9 is a graph of particulate absorption versus scan number wherein the data depicted was obtained using an absorption meter according to the present invention.

FIG. 9 shows a graph of particulate emissions versus number of scans taken with an absorption meter 10 according to the present invention. The scan number corresponds roughly to the depth of the meter at the time of the scan. This data was obtained in Puget Sound, Wash., U.S.A., by lowering the absorption meter into the ocean to an approximate depth of about 1.5 to about 20 meters. This particular absorption meter 10 was sampling at 7 Hz. FIG. 9 provides a chlorophyll a absorption profile (hence concentration) data in situ heretofore impossible to achieve with a fluorometer. Moreover, the depth profile provides data on changes in depth on the order of only about one centimeter. Fluorometers have a large time constant on the order of about one second to about three seconds, which is far larger than that of the absorption meter used for this test. Therefore, if a fluorometer had been used to profile the chlorophyll and was lowered at the same rate as the absorption meter, the fluorometer would have only obtained a fraction (about every twenty-first data point) of the data points obtained by the absorption meter. If a fluorometer was lowered at a slower rate, ship drift would introduce error into the depth profile.

Figure 10:
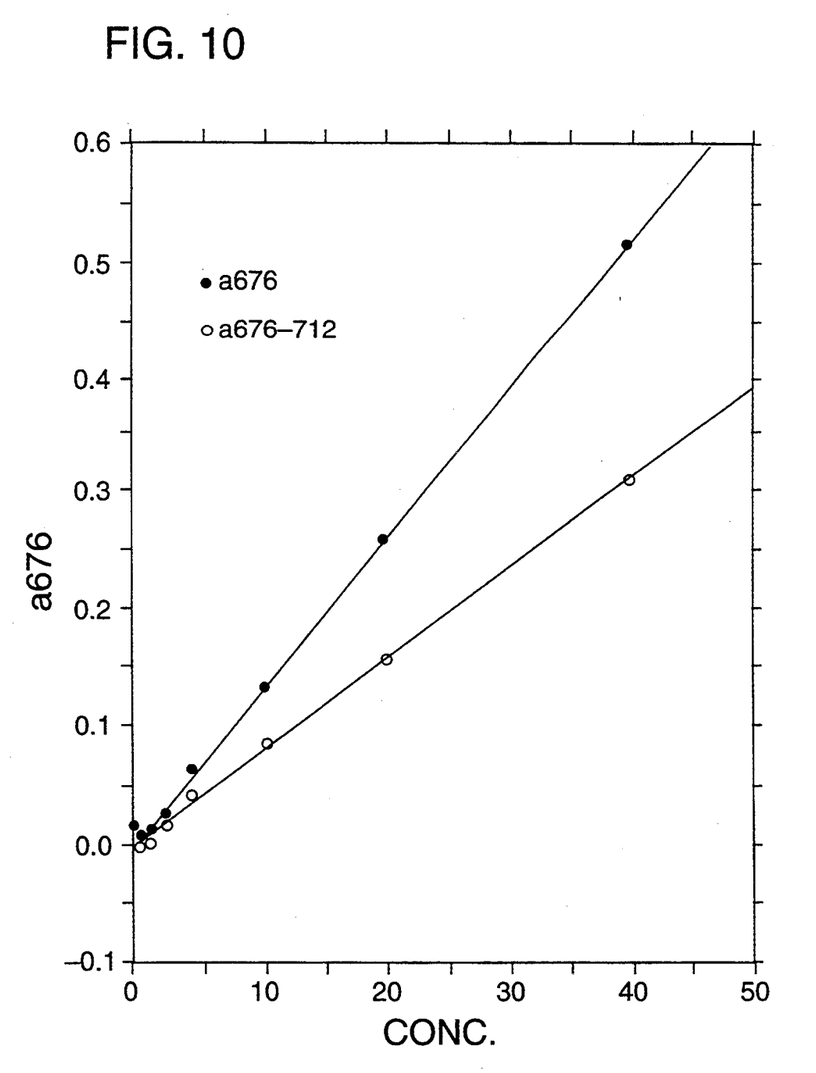
FIG. 10 is a graph of the absorption coefficient at 676 nm versus concentration wherein the data depicted was obtained using an absorption meter according to the present invention.

FIG. 10 is a graph illustrating data that can be obtained to calibrate a meter 10 according to the present invention. The meter 10 is capable of determining the concentration of dissolved substances, and that information can be used to calibrate the meter 10. The straight line labelled a676 is absorption coefficient data versus concentration measured at 676 nm, whereas the line labelled a676-712 is a straight line plot of the difference between the absorption coefficient data for the two wavelengths of interest in determining chlorophyll concentration. The a676-712 plot can also be used to determine the concentration of an unknown sample. This can be done by determining the difference between the absorption coefficients for the 676 nm wavelength and the 712 nm wavelength absorption and then comparing the result to the straight line plot.

Having illustrated and described the principles of the invention in a preferred embodiment, it should be apparent to those skilled in the art that the invention can be modified in arrangement and detail without departing from such principles. We claim all modifications coming within the spirit and scope of the following claims.

I claim:

1. A chlorophyll absorption meter for measuring in situ the concentration of chlorophyll in a liquid, comprising:
   a pressure case, the case protecting the meter from damage resulting from immersion in a liquid;
   a light source located inside the pressure case for generating light at a first wavelength of about 675 nanometers and at a second wavelength of from about 710 nanometers to about 725 nanometers;
   a liquid sample receiver, located outside the pressure case and positioned to receive light from the light source, the sample receiver having a liquid inlet and a liquid outlet port, that continuously receives a liquid sample;
   a signal detector located inside the pressure case for detecting light at the first and second wavelengths after the light is transmitted through the liquid sample in the sample receiver, the light source and the signal detector being separated to provide a region therebetween for the sample receiver to receive the liquid sample; and
   means for determining a difference between absorption values at the first and second wavelengths, the means for determining the difference being connected to the detector and adapted to receive signals from the detector.

2. The meter according to claim 1 wherein the light source includes first and second filters that transmit light at the first and second wavelengths.

3. The meter according to claim 2 wherein the second filter transmits light having a wavelength of about 712 nanometers.

4. The meter of claim 1 wherein the light source further comprises:
   a plurality of filters located inside the pressure case and positioned between the light source and the liquid sample receiver; and
   a filter selector for selecting filters from the plurality of filters in a controlled sequence.

5. The meter of claim 4 wherein the plurality of filters include a first and second filter that transmit light having wavelengths of about 675 manometers and 712 nanometers, respectively.

6. The meter according to claim 1 wherein the light source comprises a plurality of light emitting diodes.

7. The meter according to claim 6 wherein the plurality of light emitting diodes includes a first diode that emits light having a wavelength of about 675 nanometers, and a second diode that emits light having a wavelength of from about 710 to about 725 nanometers.

8. The meter according to claim 7 wherein the second diode emits light having a wavelength of about 712 nanometers.

9. A meter for measuring liquid chlorophyll concentrations in situ, the meter comprising:
   a water-tight pressure case, the case protecting the meter from wetting and pressure damage that may result from immersing the meter in water;
   a light source located inside the pressure case for generating light of selected wavelengths including a first wavelength of about 675 nanometers and a second wavelength of about 710 to about 725 nanometers;
   a signal detector located inside the pressure case for detecting light after it is transmitted through the liquid;
   means for determining a difference between absorption values at the first and second wavelengths, the means for determining a difference being connected to the detector and adapted to receive signals from the detector; and
   a sample receiver located inside the pressure case for positioning a liquid sample between the light source and the signal detector, the sample receiver having a sample inlet and a sample outlet for continuously receiving a liquid sample in situ.

10. The meter according to claim 9 wherein the light source includes a light filter that permits wavelengths of about 712 nanometers to pass therethrough so that the second wavelength is about 712 nanometers.

11. The meter according to claim 9 wherein the pressure case can withstand pressures that result from immersion in ocean water to depths of up to about 10,000 meters.

12. A device for determining in situ the concentration of chlorophyll in a liquid, comprising:
   a pressure case, the case protecting the device from wetting and pressure damage that may result from immersing the device in a liquid;
   a light source located inside the pressure case;
   a filter wheel located inside the pressure case and between the light source and a sample receiver for selecting a particular wavelength of light, the filter wheel having a plurality of filters including a first filter that transmits light having a wavelength of about 675 nanometers, and a second filter that transmits light having a wavelength of about 710 to about 725 nanometers;
   a sample receiver located outside the pressure case, having a liquid inlet port and a liquid outlet port, that continuously receives a liquid sample, the filter wheel being located between the light source and the sample receiver;
   a reflecting tube located inside the sample receiver that surrounds the liquid sample, the tube defining a channel of known pathlength for receiving liquid from the inlet port, the tube having inner walls that reflect scattered light transmitted through a liquid sample;
   a signal detector located inside the pressure case and positioned to detect the absorption signal after it is transmitted through the liquid sample; and
   a comparator connected to the detector and adapted to receive signals from the detector for determining the difference in absorption values at particular wavelengths of light.

13. The meter according to claim 12 and further comprising a beam splitter to split light into a plurality of beams.

14. The meter according to claim 13 including a reference detector placed to detect a reference beam from the beam splitter, the reference beam being transmitted to a processing unit to control a signal output from the light source.

15. The meter according to claim 12 further comprising a telemetrying device for sending an amplified signal from the signal detector to a remote location.

16. The meter according to claim 12 and further comprising display means for displaying acquired information.

17. The meter according to claim 12 and further comprising control means for controlling the operation of the meter.

18. A method for determining the concentration of chlorophyll in a liquid, comprising:
    transmitting through a liquid sample light at a first wavelength of about 675 nanometers;
    measuring the amount of light transmitted through the liquid sample at 675 nanometers;
    transmitting light through the liquid at a second wavelength of from about 710 to about 725 nanometers;
    measuring the amount of light transmitted through the liquid sample at from about 710 to about 725 nanometers;
    calculating an absorption coefficient from the amounts of light transmitted at the two wavelengths; and
    calculating the difference between light absorbed by the liquid sample at 675 nanometers and light absorbed by the liquid sample at from about 710 to about 725 nanometers.

19. The method according to claim 18 wherein the liquid is water.

20. A device for determining in situ the concentration of chlorophyll in water, comprising:
    a water-tight pressure case, the case protecting the device from wetting and pressure damage that may result from immersing the device in water up to depths of about 1,000 meters;
    a light source located inside the pressure case, the light source including a filter wheel that includes at least a first and second filter that transmit light having wavelengths of about 675 nanometers and 712 nanometers, respectively, the light source further including a filter selector for selecting filters from the plurality of filters in a controlled sequence;
    a beam splitter located inside the pressure case to split light from the light source into a plurality of beams;
    a reference detector located inside the pressure case and placed to detect a reference beam from the beam splitter, the reference beam being transmitted to a processing unit to compensate for optical drift in a signal output from the light source;
    a sample receiver located outside the pressure case and positioned to receive light from the light source, the receiver having a liquid inlet port and a liquid outlet port, that continuously receives a liquid sample;
    a reflecting tube located inside the sample receiver that surrounds the liquid sample, the tube defining a channel of known pathlength for receiving liquid from the inlet port, the tube having inner walls that reflect scattered light transmitted through a liquid sample;
    a signal detector located inside the pressure case positioned to detect the absorption signal after it is transmitted through the liquid sample;
    a comparator connected to the detector and adapted to receive signals from the detector for determining the difference in absorption values at particular wavelengths of light;
    display means located outside of the pressure case for displaying acquired information; and
    a telemetrying device for sending an amplified signal from the signal detector to a remote location.

* * * * *